United States Patent [19]
Wang et al.

[11] Patent Number: 5,501,727
[45] Date of Patent: Mar. 26, 1996

[54] COLOR STABILITY OF DENTAL COMPOSITIONS CONTAINING METAL COMPLEXED ASCORBIC ACID

[75] Inventors: Bing Wang, Maplewood; Sumita B. Mitra, West St. Paul, both of Minn.

[73] Assignee: Minnesota Mining and Manufacturing Company, St. Paul, Minn.

[21] Appl. No.: 202,931

[22] Filed: Feb. 28, 1994

[51] Int. Cl.$^6$ .................................................. A61K 6/00
[52] U.S. Cl. ...................... 106/35; 433/228.1; 523/116
[58] Field of Search ........................ 106/35; 433/228.1; 523/116

[56] References Cited

U.S. PATENT DOCUMENTS

| | | | |
|---|---|---|---|
| 3,898,243 | 8/1975 | Mecca | 424/273 |
| 3,954,989 | 5/1976 | Mecca | 424/273 |
| 4,211,712 | 7/1980 | Marstrand | 429/245 |
| 5,028,412 | 7/1991 | Putt et al. | 424/48 |
| 5,094,842 | 3/1992 | Riley | 424/52 |
| 5,154,762 | 10/1992 | Mitra et al. | 106/35 |

FOREIGN PATENT DOCUMENTS 335645  10/1989  European Pat. Off. .

OTHER PUBLICATIONS

Jabs et al. in *Z. Anorg. Allg. Chem.* "Titanyl Ascorbates" (1984), vol. 514, pp. 179–184 No Month.

Jabs et al. in *Z. Anorg. Allg. Chem.* "Preparation of Ascorbate Complexes of Some Elements of the First Transition Series" (1984), vol. 514, pp. 185–195 No Month.

Jabs et al. in *Inorganica Chimica Acta* "Compounds of L(+)-ascorbic acid with metals VIII. Titanium (IV) complexes of L(+)-ascorbic acid and 5,6-O-isopropylidene-L-ascorbic acid" (1990), vol. 175 pp. 273–276 No Month.

Tajimir-Riahi in *Journal of Inorganic Biochemistry* "Coordination Chemistry of Vitamin C Part III. Interaction of L-Ascorbic Acid with Al(III), La(III), and Pb(II) Ions. Evidence for Metal Chelate Formation in the Solid and Aqueous Solution" (1991), vol. 44, pp. 39–45 No Month.

*Primary Examiner*—C. Melissa Bonner
*Attorney, Agent, or Firm*—Gary L. Griswold; Walter N. Kirn; Dale A. Bjorkman

[57] ABSTRACT

A curable dental composition comprising an ethylenically unsaturated moiety, an oxidizing agent and metal complexed ascorbic acid is claimed. The incorporation of metal complexed ascorbic acid provides a curable composition that exhibits improved color stability. The metal complexed ascorbic acid is particularly useful as a component of a paste:paste glass ionomer dental cement.

21 Claims, No Drawings

COLOR STABILITY OF DENTAL COMPOSITIONS CONTAINING METAL COMPLEXED ASCORBIC ACID

BACKGROUND OF THE INVENTION

1. Field of the Invention

This invention relates to dental compositions containing metal complexed ascorbic acid. More specifically, it relates to curable dental compositions containing metal complexed ascorbic acid.

2. Description of the Background Art

Ascorbic acid (i.e., vitamin C) is a well known natural reducing agent or antioxidant. It has been utilized in combination with an oxidizing agent in nonaqueous dental systems. However, it is well recognized that ascorbic acid is easily oxidized, especially in aqueous solution, and in its oxidized or partially oxidized form exhibits a yellow to yellow/brown coloration.

Metal complexes of ascorbic acid have been prepared and characterized. Jabs et al. in *Z. Anorg. Allg. Chem.* (1984), Vol. 514, p. 179–184 describe the synthesis of ascorbate complexes of some metals of the first transition series (e.g., $TiO^{2+}$, $Cr^{3+}$, $Mn^{2+}$, $Co^{2+}$ $Ni^{2+}$ and $Zn^{2+}$) to study the biochemical mechanism of metal ion catalyzed autooxidation of pharmaceutical and naturally occurring vitamin C. The specific complexes discussed (i.e., $TiO^{2+}$ $Ni^{2+}$) were highly colored compounds.

Jabs et al. in *Z. Anorg. Allg. Chem.* (1984), Vol. 514, p. 185–195 report the electronic, infrared and $^1H$ nuclear magnetic resonance spectral characterization of titanyl ascorbates.

Jabs et al. in *Inorganica Chimica Acta* (1990), Vol. 175 p. 273–276 describe the formation of complexes of dianions when titanium(IV) halogen compounds are independently reacted with the monoalkali and dialkali metal salts of L(+)-ascorbic acid and 5,6-O-isopropylidene-L-ascorbic acid.

Tajimir-Riahi in *Journal of Inorganic Biochemistry* (1991), vol. 44, p. 39–45 report the Fourier Transform infrared and $^{13}C$ nuclear magnetic resonance spectroscopic analysis of Ai(III), La(VI) and Pb(II) ascorbates as solids and in solution.

Ascorbic acid in its complexed form has been prepared for use in medicinal and cosmetic compositions. Complexed ascorbic acid has also been incorporated in dental compositions to inhibit the formation and growth of calculus on tooth enamel.

U.S. Pat. Nos. 3,898,243 and 3,954,989 to Mecca disclose allantoin ascorbic acid complexes for use in medicinal and cosmetic compositions. The complexes are white powders and are reported to be stable in dry form and solutions and are not sensitive to heat.

U.S. Pat. No. 4,211,712 to Marstrand discloses a compound which comprises a complex combination of ascorbic acid, trivalent titanium and divalent copper. The complex compound is a brown solid used to treat diseases which present an abnormal blood picture.

U.S. Pat. No. 5,094,842 to Riley discloses oral compositions such as toothpastes which contain Vitamin C or a derivative thereof and a copper compound such as copper sulphate. Various alkali metal and alkaline earth metal salts are listed as suitable ascorbic acid derivatives. When the compositions further contain a stannous compound, they are reported to exhibit a reduced tendency to discolor upon storage and exposure to air.

U.S. Pat. No. 5,028,412 to Putt et al. discloses anticalculus oral compositions that include an aluminum salt and an aliphatic carboxylic acid or salt thereof that is capable of complexing with the aluminum. Ascorbic acid is listed, along with other carboxylic acids, as a stable preferred complexing carboxylic acid. The compositions are reported to inhibit the formation and growth of calculus on dental enamel.

SUMMARY OF THE INVENTION

The invention in one embodiment is a curable dental composition, comprising:

a) an ethylenically Unsaturated moiety, b) an oxidizing agent, and c) metal complexed ascorbic acid.

The invention in another embodiment is a water containing, ionically hardenable dental composition, comprising:

a) finely divided reactive filler, b) an acidic water miscible polymer, c) an ethylenically unsaturated moiety, d) an oxidizing agent, and e) metal complexed ascorbic acid.

A preferred embodiment of the invention is a glass ionomer paste:paste composition containing metal complexed ascorbic acid as the reducing agent. The incorporation of metal complexed ascorbic acid provides a composition that exhibits improved color stability.

DETAILED DESCRIPTION

Applicants have surprisingly found that when ascorbic acid is present as a metal complex in curable dental compositions, the resultant compositions are color stable without loss of the excellent reducing capabilities of ascorbic acid. The curable dental compositions of the invention can be mixed and clinically applied using conventional techniques. The compositions have general applicability as restoratives, liners, bases, cements, sealants and as dental or orthodontic adhesives.

In a preferred embodiment, a tri-cure glass ionomer cement, the three-way cure mechanism facilitates thorough, uniform cure and retention of good clinical properties. The cements of the invention provide utility for all the applications enumerated above, but have particular utility in clinical applications where cure of a conventional light-curable composition may be difficult to achieve. Such applications include deep restorations, large crown build-ups, endodontic restorations, luting of metallic crowns or other light-impermeable prosthetic devices to teeth, and other restorative applications in inaccessible areas of the mouth.

A particularly preferred embodiment of the invention is a glass ionomer cement in the form of a two part paste:paste formulation; however, formulations composed of more than two parts can be used. Two part paste:paste systems are particularly convenient and easy for the practitioner to use.

A dental composition containing metal complexed ascorbic acid exhibits improved color stability when compared to a similar composition containing unmodified ascorbic acid. This is observed when the $\Delta E^*_{ab}$ value of a cured composition containing metal complexed ascorbic acid is less than that of a similar composition containing unmodified ascorbic acid.

The color stability of a material is evaluated by measuring in reflection the L*, a* and b* color coordinates of a cured sample containing complexed ascorbic acid and a similar sample containing unmodified ascorbic acid. The color coordinates are obtained by the CIELAB (CIE 1978) color determination methods described in Billmeyer & Saltzman, *Principles of Color Technology.*, 2nd Ed., pp. 62–65 (1981). The $\Delta L^*$, $\Delta a^*$ and $\Delta b^*$ values are obtained by subtracting the L*, a* and b* values of a cured sample of the aged material containing the complexed ascorbic acid from the L*, a* and b* values of a cured sample of the same material immediately after it has been formulated.

The $\Delta E^*_{ab}$ values are obtained using the CIELAB color difference equation set out in Billmeyer & Saltzman, id. at p. 103. The sample is considered to exhibit color stability if the $\Delta E^*_{ab}$ value of the cured sample after aging at 45° C. for 5 days is less than the $\Delta E^*_{ab}$ value of a similar sample containing unmodified ascorbic acid. More preferably, the sample is considered to exhibit color stability if the $\Delta E^*_{ab}$ value of the cured sample after aging at 45° C. for 5 days is less than about 5 and most preferably less than about 3.

The curable dental composition of the invention, in the broadest embodiment, contains three components. The components are an ethylenically unsaturated moiety, an oxidizing agent and metal complexed ascorbic acid.

The first component of the dental composition of the invention is an ethylenically unsaturated moiety. The ethylenically unsaturated moiety can be present as a separate ingredient (for example, as an acrylate- or methacrylate-functional monomer) or it can, if desired, be present as a group on another ingredient. The ethylenically unsaturated moiety can be present as a single component or as a mixture of components. A wide variety of ethylenically unsaturated moieties can be used. A useful list of suitable materials is presented at column 5, line 43 through column 7, line 23 of U.S. Pat. No. 5,063,257. Of the many materials mentioned, water miscible or water soluble acrylates and methacrylates such as 2-hydroxyethyl methacrylate, hydroxymethyl methacrylate, 2-hydroxypropyl methacrylate, tetrahydrofurfuryl methacrylate, glycerol mono- or dimethacrylate, trimethylol propane trimethacrylate, ethylene glycol dimethacrylate, polyethylene glycol dimethacrylate, urethane methacrylates, acrylamide, methacrylamide, methylene bis-acrylamide or methacrylamide, and diacetone acrylamide and methacrylamide are preferred. Mixtures of ethylenically unsaturated moieties can be used if desired. Additional monomers, oligomers and polymers may also be present. In a preferred embodiment, the ethylenically unsaturated moieties are present as groups on the acidic polymer, as described in more detail below.

The second and third components of the dental composition of the invention are an oxidizing agent and metal complexed ascorbic acid reducing agent. The oxidizing agent and the metal complexed ascorbic acid are the redox catalyst system that enable the dental composition to cure via a redox reaction.

The oxidizing agent should react with or otherwise cooperate with the metal complexed ascorbic acid reducing agent to produce free radicals capable of initiating polymerization of the ethylenically unsaturated moiety. The oxidizing agent and the metal complexed ascorbic acid preferably are sufficiently shelf stable and free of undesirable coloration to permit their storage and use under typical dental conditions. The oxidizing agent and the metal complexed ascorbic acid should also preferably be sufficiently soluble and present in an amount sufficient to permit an adequate free radical reaction rate. This can be evaluated by combining the ethylenically unsaturated moiety, the oxidizing agent and the metal complexed ascorbic acid and observing whether or not a hardened mass is obtained.

Suitable oxidizing agents include persulfates such as sodium, potassium, ammonium and alkyl ammonium persulfates, benzoyl peroxide, hydroperoxides such as cumene hydroperoxide, tert-butyl hydroperoxide, tert-amyl hydroperoxide and 2,5-dihydroperoxy-2,5-dimethylhexane, salts of cobalt (III) and iron (III), hydroxylamine, perboric acid and its salts, salts of a permanganate anion, and combinations thereof. Hydrogen peroxide can also be used, although it may, in some instances, interfere with the photoinitiator, if one is present. It is particularly preferred to use the oxidizing agent in an encapsulated form as described in U.S. Pat. No. 5,154,762.

Metal complexed ascorbic acid is the reducing agent. The metal complexed ascorbic acid provides a dental composition that exhibits color stability and maintains the catalytic potency of the ascorbic acid. Any metallic ion that can form stable complexes with ascorbic acid can be used. Preferred metals include the transition metals and metals of group IA, IIA, and IIIB. Particularly preferred complexing metals are zirconium and aluminum with aluminum being most preferred. The desired metal complexed ascorbic acid is preferably prepared using a suitable metal alkoxide or metal salt.

The metal complexed ascorbic acid can be added to the dental composition in its powdered form or it can be precipitated as a coating on a filler, e.g., zirconium oxide, silica, ceramic fillers and fluoroaluminosilicate glass. It is preferred to add the metal complexed ascorbic acid in its powdered form.

The amounts of the metal complexed ascorbic acid reducing agent and the oxidizing agent should be sufficient to provide the desired degree and rate of polymerization of the ethylenically unsaturated component. The preferred amount for each of the metal complexed ascorbic acid and the oxidizing agent is about 0.01 to about 10%, more preferably about 0.02 to about 5%, based on the total weight of the uncured composition.

Optionally, the curable dental composition may contain a photoinitiator. The photoinitator should be capable of promoting free radical crosslinking of the ethylenically unsaturated moiety on exposure to light of a suitable wavelength and intensity. It also preferably is sufficiently shelf stable and free of undesirable coloration to permit its storage and use under typical dental conditions. Visible light photoinitiators are preferred. The photoinitiator preferably is water soluble or water miscible. Photoinitiators bearing polar groups usually have a sufficient degree of water solubility or water miscibility. The photoinitiator frequently can be used alone, but typically it is used in combination with a suitable donor compound or a suitable accelerator (for example, amines, peroxides, phosphorus compounds, ketones and alpha-diketone compounds).

Preferred visible light-induced initiators include camphorquinone (which typically is combined with a suitable hydrogen donor such as an amine), diaryliodonium simple or metal complex salts, chromophore-substituted halomethyl-s-triazines and halomethyl oxadiazoles. Particularly preferred visible light-induced photoinitiators include combinations of an alpha-diketone, e.g., camphorquinone, and a diaryliodonium salt, e.g., diphenyliodonium chloride, bromide, iodide or hexafluorophosphate, with or without additional hydrogen donors (such as sodium benzene sulfinate, amines and amine alcohols).

Preferred ultraviolet light-induced polymerization initiators include ketones such as benzyl and benzoin, and acyloins and acyloin ethers. Preferred commercially available ultraviolet light-induced polymerization initiators include 2,2-dimethoxy-2-phenylacetophenone ("IRGACURE 651") and benzoin methyl ether (2-methoxy-2-phenylacetophenone), both from Ciba-Geigy Corp.

The photoinitiator should be present in an amount sufficient to provide the desired rate of photopolymerization. This amount will be dependent in part on the light source, the thickness of the layer to be exposed to radiant energy, and the extinction coefficient of the photoinitiator. Typically, the photoinitiator components will be present at a total weight of about 0.01 to about 5%, more preferably from about 0.1 to about 5%, based on the total weight of the composition.

The curable dental composition of the invention optionally can contain non-reactive fillers, reactive fillers, water, stabilizers, pigments, coupling agents, viscosity modifiers, accelerators, inhibitors, medicaments, and other ingredients that will be apparent to those skilled in the art.

A preferred embodiment of the invention is a glass ionomer dental composition comprising finely divided reactive filler, acidic water miscible polymer, an ethylenically unsaturated moiety, an oxidizing agent and metal complexed ascorbic acid. Unmodified ascorbic acid is present as the reducing agent in a dental cement composition disclosed in U.S. Pat. No. 5,154,762 assigned to the assignee of the present invention. The ascorbic acid in combination with an oxidizing agent provides a tri-cure cement, i.e., a cement having three curing modes, namely a redox initiated curing mechanism in addition to an acid-filler ionic curing mechanism and a photoinitiated free radical crosslinking curing mechanism. The incorporation of the redox initiated curing mechanism provides a cement that cures well in thick layers and can be used without a dental curing light or with a light that is weak or defective.

The aforementioned cement is commercially available as a powder:liquid formulation. The powder contains ascorbic acid which is microencapsulated to ensure its stability prior to admixture with the liquid. While powder:liquid glass ionomer cements have been widely accepted, there are certain drawbacks insofar as the practitioner must measure out the powder and the liquid prior to use. In particular, for restorative applications, a relatively large amount of a somewhat flocculent powder must be hand spatulated with a relatively small amount of liquid. This may be not only inconvenient but also time consuming for a busy dental practitioner. Hence, the desire to provide the practitioner with a paste:paste system, which, in general, is more convenient to use than a powder:liquid or a liquid:paste system.

The cements of the invention are not limited to paste:paste formulations. For example, traditional powder:liquid formulations as well as paste:liquid formulations can be prepared. These formulations generally are two-part systems and are prepared by hand spatulating the parts together. Other useful configurations will be familiar to those skilled in the art.

The glass ionomer cement of the invention contains water. The water can be distilled, deionized or plain tap water. Generally, deionized water is preferred. The amount of water should be sufficient to provide adequate handling and mixing properties and to permit the transport of ions in the filler-acid reaction. Preferably, water represents at least about 1%, more preferably about 3% to about 25%, and most preferably about 5% to about 20% of the total weight of ingredients used to form the cement.

The glass ionomer cement of the invention is ionically hardenable. By this is meant that it contains ingredients that, when combined, can react via an ionic reaction to produce a hardened mass. The ionic reaction occurs between acid groups on the polymer and acid-reactive groups on the filler.

The first component of the glass ionomer cement is finely divided reactive filler. The filler should be sufficiently finely-divided so that it can be conveniently mixed with the other ingredients and used in the mouth. Preferred average particle diameters for the filler are about 0.2 to about 15 micrometers, more preferably about 1 to 10 micrometers, as measured using, for example, a sedimentation analyzer.

Preferred fillers are acid-reactive. Suitable acid-reactive fillers include metal oxides, metal salts and glasses. Preferred metal oxides include barium oxide, calcium oxide, magnesium oxide and zinc oxide. Preferred metal salts include salts of multivalent cations, for example aluminum acetate, aluminum chloride, calcium chloride, magnesium chloride, zinc chloride, aluminum nitrate, barium nitrate, calcium nitrate, magnesium nitrate, strontium nitrate and calcium fluoroborate. Preferred glasses include borate glasses, phosphate glasses and fluoroaluminosilicate glasses. Fluoroaluminosilicate glasses are particularly preferred. Suitable fillers are also available from a variety of commercial sources familiar to those skilled in the art. For example, suitable fillers can be obtained from a number of commercially available glass ionomer cements, such as "GC Fuji LC" cement and "Kerr XR" ionomer cement. Mixtures of fillers can be used if desired.

If desired, the filler can be subjected to a surface treatment. Suitable surface treatments include acid washing, treatment with phosphates, treatment with chelating agents such as tartaric acid, treatment with a silane coupling agent.

The amount of filler should be sufficient to provide a cement having desirable mixing and handling properties before cure and good cement performance after cure. Preferably, the filler represents less than about 90%, more preferably about 25% to about 85%, and most preferably about 75% to about 85% by weight of the total weight (including water) of the unset cement components.

The second component of the glass ionomer cement of the invention is an acidic, water miscible polymer. The acidic polymer should be at least sufficiently water miscible so that it does not undergo substantial sedimentation when combined with the liquid ingredients of the cement, but need not be entirely water soluble. Suitable acidic polymers include those listed at column 2, line 62 through column 3, line 6 of U.S. Pat. No. 4,209,434. Preferred acidic polymers include homopolymers and copolymers of alkenoic acids such as acrylic acid, itaconic acid and maleic acid. Suitable polymers are also available from a wide variety of commercial sources, and many are found in currently-available glass ionomer cements. As will be appreciated by those skilled in the art, the polymer should have a molecular weight sufficient to provide good storage, handling and mixing properties. A preferred molecular weight is about 5000 to about 100,000 weight average molecular weight ($\overline{M}_w$), evaluated against a polystyrene standard using gel permeation chromatography.

The third component of the glass ionomer cement of the invention is an ethylenically unsaturated moiety as discussed above. The ethylenically unsaturated moiety and the acidic polymer may be present as separate components or as a mixture of components. Preferably the ethylenically unsaturated moiety is present on the acidic polymer. Other monomers, oligomers and polymers may also be present.

Suitable ethylenically unsaturated acidic polymers are described in U.S. Pat. Nos. 4,872,936 and 5,130,347. Preferably, the numbers of acid groups and ethylenically unsaturated groups are adjusted to provide an appropriate balance of properties in the cement, both during the setting reaction and after the cement has hardened. Acidic polymers in which about 10 to about 30% of the acidic groups have been replaced with ethylenically unsaturated groups are preferred.

The amount of acidic polymer in the cement should also be sufficient to provide a desired balance of physical properties. A preferred acidic polymer amount is at least about 5%, more preferably about 10 to about 50%, and most preferably about 10 to about 30% of the total weight (including water) of the unset cement components.

The fourth and fifth components of the glass ionomer cement of the invention are the oxidizing agent and the metal complexed ascorbic acid. These component have been discussed in detail above.

Optionally, the glass ionomer cement may contain stabilizers. Stabilizers are particularly useful for paste:paste formulations. The incorporation of stabilizers serves to further improve the color stability of metal complexed ascorbic acid containing paste:paste compositions. Suitable stabilizers include oxalic acid, sodium metabisulfite, metaphosphoric acid, sodium bisulfite, sodium thiosulfate, and combinations thereof. Oxalic acid and sodium metabisulfite are preferred stabilizers.

If desired, the cements of the invention can contain adjuvants such as pigments, nonvitreous fillers, inhibitors, accelerators, viscosity modifiers, medicaments and other ingredients that will be apparent to those skilled in the art.

The invention will be further clarified by consideration of the following non-limiting examples, which are intended to be purely exemplary of the invention. All parts and percentages are by weight unless otherwise indicated.

PREPARATORY EXAMPLE 1

Aluminum Ascorbate, Molar Ratio Ascorbic Acid Aluminum=2:1

Ascorbic acid (10 g, 0.07 moles) was dissolved in 150 ml of methanol. Aluminum butoxide (7 g, 0.035 moles) in 10 ml of isopropanol was added slowly to the ascorbic acid:methanol solution. After addition was complete, the mixture was stirred for 30 minutes with some precipitate observed. Water (10 ml) was then added and the solution stirred for 2 hours. Finally, 100 ml of ethyl acetate was added to precipitate aluminum ascorbate. The aluminum ascorbate was filtered, washed with water and then methanol. The infrared spectrum showed that the carbonyl peak had shifted from 1675 $cm^{-1}$ for unmodified ascorbic acid to 1625 $cm^{-1}$ for the aluminum ascorbate.

PREPARATORY EXAMPLE 2

Zirconium Ascorbate, Molar Ratio Ascorbic Acid:Zirconium=1.7:1

Ascorbic acid (10 g, 0.0567 moles) was dissolved in 200 ml of methanol. Zirconium n-propoxide (70% in n-propanol, 15 ml, 0.0333 moles) was slowly added to the ascorbic acid:methanol solution. After addition was complete, 5 ml of water was added to the resultant solution to catalyze hydrolysis and condensation of zirconium n-propoxide to zirconium oxide. The solution was stirred for 1 hour before the methanol was distilled off. The precipitate was filtered and washed with water to remove any free ascorbic acid. The white powder was dried in a 45° C. oven under vacuum for 24 hours.

PREPARATORY EXAMPLE 3

Zirconium Ascorbate, Molar Ratio Ascorbic Acid: Zirconium=2.5:1

Ascorbic acid (2 g, 0.014 moles) was dissolved in 50 ml of methanol. Zirconium n-propoxide (70% in n-propanol, 2.56 ml, 0.00569 moles) was slowly added to the ascorbic acid:methanol solution. After addition was complete, the mixture was stirred for 30 minutes with some precipitate observed. The methanol was distilled off to yield zirconium ascorbate as a white powder. The powder was dried in a 45° C. oven for 24 hours.

PREPARATORY EXAMPLE 4

Zirconium Ascorbate Molar Ratio Ascorbic Acid:Zirconium=0.5:1

The procedure of PREPARATORY EXAMPLE 3 was repeated, except 1.28 ml (0.00285 moles) instead of 2.56 ml (0.00569 moles) of zirconium n-propoxide (70% in n-propanol) was added to the ascorbic acid:methanol solution.

PREPARATORY EXAMPLE 5

Zirconium Ascorbate Coated on Zirconium Oxide

Ascorbic acid (40 g) was dissolved in 600 ml of methanol. Zirconium n-propoxide (70% in n-propanol, 60 ml) was slowly added to the ascorbic acid:methanol solution. After addition was complete, the mixture was stirred for 10 minutes with some precipitate observed. Then 60 ml of water was added and the resultant mixture stirred for 2 hours at which time 100 g of zirconium oxide was added and the resultant mixture stirred overnight. The zirconium ascorbate deposited on the zirconium oxide and was isolated by filtration and washed with water.

PREPARATORY EXAMPLE 6

Treated Fluoroaluminosilicate Glass

The ingredients set out below in TABLE I were mixed, melted in an arc furnace at about 1350°–1450° C., poured from the furnace in a thin stream and quenched using chilled rollers to provide an amorphous single-phase fluoroaluminosilicate glass.

TABLE I

| Ingredient | Parts |
| --- | --- |
| $SiO_2$ | 37 |
| $AlF_3$ | 23 |
| $SrO$ | 20 |
| $Al_2O_3$ | 10 |
| $AlPO_4$ | 7 |
| $Na_3AlF_6$ | 6 |
| $P_2O_5$ | 4 |

The glass was ball-milled to provide a pulverized frit with a surface area of 2.5-3.2 $m^2/g$ measured using the Brunauer, Emmet and Teller (BET) method.

A silanol solution was prepared by mixing together 2.0 parts gamma-methacryloxypropyl trimethoxysilane ("A-174" Union Carbide Corp), 12.6 parts methanol, 12.6 parts water and 0.22 parts acetic acid. The mixture was stirred magnetically for 30 minutes at ambient temperature, added to 50 parts of the glass powder and slurried for 1.5 hours at ambient temperature. The slurry was poured into a plastic-lined tray and dried for 20 hours at 45° C. The silanol treated dried powder was sieved through a 74 micron mesh screen.

PREPARATORY EXAMPLE 7

Treated Zirconia:Silica Filler 25.5 Parts silica sol("LUDOX" LS, E.I. dupont de Nemours & Co.) were acidified by the rapid addition of 0.255 parts concentrated nitric acid. In a separate vessel, 12.9 parts ion-exchanged zirconyl acetate (Magnesium Elecktron Inc.) were diluted with 20 parts deionized water and the resultant solution acidified with 0.255 parts concentrated nitric acid. The silica sol was pumped into the stirred zirconyl acetate solution and mixed for one hour while filtering the stirred mixture through "CUNO" 5 micrometer and 1 micrometer filters (Commercial Intertech Corp.). The stirred, filtered mixture was further filtered though a 1 micrometer "HYTREX" filter (Osmonics, Inc.) followed by a 0.22 micrometer "BALSTRON" filter (Balston Inc.). The filtrate was poured into trays to a depth of about 25 mm and dried at 65° C. in a forced air oven for about 24 hours. The resultant dried material was removed from the oven and tumbled through a rotary tube furnace (Harper Furnace Corporation) preheated to 600° C. 21 Parts of calcined microparticles were obtained. The calcined microparticles were comminuted in a tumbling ball mill until all of the microparticles were less than 10 micrometers in particle diameter. 0.3 Part portions of the milled microparticles were placed in ceramic saggers and fired in an electric kiln (Harper Furnace Corporation) in air at 825° C. for 1 hour. The fired microparticles were allowed to cool in air. The cooled microparticles were slurried in hydrolyzed A-174 silane, dried in a forced air oven and screened through a 74 micrometer screen. The treated filler particles contained 11.1% silane.

EXAMPLE 1

The ingredients set out below in TABLE II were combined to form a Paste "I".

TABLE II

| Ingredient | g |
| --- | --- |
| Filler of PREP. EX. 7 | 65 |
| Copolymer[1] | 13 |
| GDMA[2] | 9 |
| Bis-GMA | 6 |
| Water[3] | 7 |
| Complexed AA (See TABLE IIa) | 0.32 |

[1]Ethylenically unsaturated acidic copolymer prepared like the precipitated dry polymer of EXAMPLE 11 of U.S. Pat. No. 5,130,347
[2]Glycerol dimethacrylate
[3]Deionized water Four Paste I formulations, Ia, Ib, Ic and Id, were independently prepared using the metal complexed ascorbic acid set out below in TABLE IIa. Each Paste I formulation was hand-loaded into an opaque polyethylene syringe and aged at 45° C. for 14 days. On day 14, the syringes were removed from the oven and a sample of each aged paste and its corresponding unaged paste were syringed side by side on a white paper towel.

Set out below in TABLE IIa are the specific metal complexed ascorbic acid added to each paste I along with the visual color change observation after aging the pastes at 45° C. for 14 days.

TABLE IIa

| Paste | Complexed Ascorbic Acid | Color |
| --- | --- | --- |
| Ia | PREPARATORY EXAMPLE 2 | Pale Yellow |
| Ib | PREPARATORY EXAMPLE 3 | Yellow |
| Ic | PREPARATORY EXAMPLE 4 | Yellow |
| Id | PREPARATORY EXAMPLE 4; CAB Encapsulated* | Light Yellow |

*Microencapsulation in cellulose acetate butyrate prepared using the procedure of EXAMPLE 11 of U.S. Pat. No. 5,154,762

The data in TABLE IIa show that, upon visual inspection, the Paste Ia formulation containing zirconium ascorbate (molar ratio of ascorbic acid:zirconium of 1.7:1) showed the greatest color stability on accelerated aging. Therefore, it would be the formulation best suited for use in a dental composition.

EXAMPLE 2

The Paste I formulations of TABLE IIa were prepared with the addition of 0.65 g sodium metabisulfite and/or 0.65 g oxalic acid stabilizers. The resultant pastes were aged at 45° C. for 7 days. The visual color change observation was determined as detailed in EXAMPLE 1.

Set out below in TABLE III are the run no., the Paste I formulation from TABLE IIa, the stabilizer added to each Paste I and the visual color change observation after aging the pastes at 45° C. for 7 days.

TABLE III

| Run No. | Paste I Composition | Stabilizer | Color |
| --- | --- | --- | --- |
| 1 | Id | $Na_2S_2O_5$ | Yellow |
| 2 | Ib | $Na_2S_2O_5$ | Light Yellow |
| 3 | Ic | $Na_2S_2O_5$ | Yellow |
| 4 | Ia | $Na_2S_2O_5$ | Pale Yellow |
| 5 | Ib | Oxalic Acid | Light Yellow |
| 6 | Ic | Oxalic Acid | Yellow |
| 7 | Ia | Oxalic Acid | Light Yellow |
| 8 | Ib | $Na_2S_2O_5$ + OA* | Almost No Change |
| 9 | Id | $Na_2S_2O_5$ + OA | Almost No Change |
| 10 | Ia | $Na_2S_2O_5$ + OA | No Change |

*Oxalic acid

The data in TABLE III show that the greatest degree of color stability was maintained in the paste compositions containing both sodium metabisulfite and oxalic acid (Run nos. 8–10). The formulation maintaining the greatest degree of color stability (i.e., Ia) was prepared with zirconium ascorbate having a molar ratio of ascorbic acid:zirconium of 1.7:1.

EXAMPLE 3

Paste Ia formulations from TABLE IIa were prepared with the addition of 0.65 g sodium metabisulfite and/or 0.65 g oxalic acid stabilizers as well as without the addition of stabilizer. The resultant Paste Ia formulations were mixed with an equal amount of a Paste "II" designated Paste IIa, prepared by combining the ingredients set out below in TABLE IV.

TABLE IV

| Ingredient | % |
| --- | --- |
| Glass of PREP. EX. 6 | 72.62 |
| Zirconium fluoride | 12.40 |
| GDMA | 2.15 |
| HEMA[1] | 6.91 |
| Bis-GMA | 5.23 |
| $K_2S_2O_8$ CAB Encapsulated[2] | 0.40 |
| DPI[3] | 0.17 |
| CPQ[4] | 0.10 |
| BHT[5] | 0.02 |

[1] 2-Hydroxyethyl methacrylate
[2] Microencapsulation in cellulose acetate butyrate prepared according to the procedure of EXAMPLE 9 of U.S. Pat. No. 5,154,762
[3] Diphenyliodonium hexafluorophosphate
[4] Camphorquinone
[5] Butylated hydroxytoluene The set times of the Paste Ia:Paste IIa compositions were measured according to ISO specification 9917. The average set time of all samples prepared immediately after formulation and before aging was 1'30" to 1'40".

The Paste Ia:Paste IIa formulations were formed into 1 mm thick disks by pressing each Paste Ia:Paste IIa mixture into a 1 mm thick×2 cm diameter steel mold. Each disk was cured with a "VISILUX 2" dental curing light (3M) using a 60 second exposure to each side of the sample, and a 1 cm distance between the output end of the light guide and the sample.

Each cured disk was removed from the mold and placed in a 37° C./95% relative humidity chamber for 15 to 30 minutes. Each disk was removed from the chamber and stored in deionized water at room temperature for 15 to 60 minutes. Then each disk was removed from the water, blotted dry with a paper towel and color coordinates immediately measured.

The color coordinates for standard daylight conditions were measured for each disk using a "DINO MATCH SCAN II" color computer (Bausch & Lomb Inc.) with a 25 mm diameter sample port. The L*, a* and b* reflection color coordinates were obtained using the standard white color tile in the reflection sample port.

Each syringe containing the remainder of Paste Ia was aged at 45° C. for various time intervals. Each Paste Ia formulation was mixed with an equal amount of Paste IIa, disks were prepared and color coordinates measured as detailed for the samples prepared immediately after formulation.

The ΔL*, Δa* and Δb* values were obtained by subtracting the L*, a* and b* values of a cured sample of the aged material from the L*, a* and b* values of a cured sample of the same material immediately after it has been formulated. The $\Delta E^*_{ab}$ values are reported in TABLE V.

Set out below in TABLE V are the run no., the stabilizer added to each Paste Ia, the set time of the Paste Ia:Paste IIa compositions at 37° C. the length of time the Paste Ia formulations were aged at 45° C. and the $\Delta E^*_{ab}$ color value for each Paste Ia:Paste IIa composition.

TABLE V

| Run No. | Stabilizer | Set Time (37° C.) | Days (45° C.) | $\Delta E_{ab}^*$ |
| --- | --- | --- | --- | --- |
| 1 | None | — | 3 | 5.29 |
|   |      | — | 9 | 9.8 |
| 2 | Oxalic Acid | 1'50" | 3 | 3.66 |
|   |             | 2'10" | 9 | 13.70 |
| 3 | $Na_2S_2O_5$ | 1'40" | 3 | 2.71 |
|   |              | 2'10" | 9 | 8.24 |
| 4 | OA* + $Na_2S_2O_5$ | 1'50" | 3 | 1.74 |
|   |                    | 2'    | 9 | 1.40 |

*Oxalic acid

The data in TABLE V show the improvement in color stability with no significant change in set time of a dental composition containing metal complexed ascorbic acid as well as stabilizers. Even after 9 days at 45° C., the composition of Run no. 4 exhibited excellent color stability with only a slight increase in set time.

EXAMPLE 4

Two Paste I formulations were prepared as in TABLE II except that instead of the 0.32 g metal complexed ascorbic acid, 0.8 g of the aluminum ascorbate of PREPARATORY EXAMPLE 1 was incorporated in Paste Ie and 1.6 g of the zirconium ascorbate coated on zirconium oxide of PREPARATORY EXAMPLE 5 was incorporated in Paste If. Additionally, both Paste Ie and Paste If contained both 1 g oxalic acid and 1 g sodium metabisulfite stabilizers.

Paste Ie and Paste If were independently mixed with an equal amount of Paste IIa of TABLE IV, disks were prepared and color coordinates were measured as described in EXAMPLE 3.

Paste Ie and Paste If were then aged at 45° C. for 6 and/or 9 days. Aged Paste Ie and Paste If were independently mixed with an equal amount of Paste IIa of TABLE IV, disks were prepared and color coordinates measured as detailed in EXAMPLE 3.

Set out below in TABLE VI are the Paste I composition, the length of time the Paste I was aged at 45° C. and the $\Delta E^*_{ab}$ color value for each Paste I:Paste IIa composition.

TABLE VI

| Paste I Composition | Days (45° C.) | $\Delta E_{ab}^*$ |
| --- | --- | --- |
| Ie | 6 | 1.1 |
| Ie | 9 | 2.41 |
| If | 9 | 5.75 |

The data in TABLE VI show that the color stability of the paste:paste composition containing aluminum ascorbate (i.e., Paste Ie) was superior to a similar composition containing zirconium ascorbate coated on zirconium oxide filler (i.e., Paste If).

EXAMPLE 5

The ingredients set out below in TABLE VII were combined to form Paste Ig.

TABLE VII

| Ingredient | g |
| --- | --- |
| Filler of PREP. EX. 7 | 16.25 |
| Copolymer[1] | 6.324 |
| GDMA[2] | 1.97 |

TABLE VII-continued

| Ingredient | g |
| --- | --- |
| Oxalic Acid | 0.163 |
| $Na_2S_2O_5$ | 0.163 |
| Ascorbic Acid (Unmodified) | 0.13 |

[1] Ethylenically unsaturated acidic copolymer prepared like the precipitated dry polymer of EXAMPLE 11 of U.S. Pat. No. 5,130,347 containing 26.4% water, 20% HEMA, 6.5% 1-tartaric acid and 0.1% BHT
[2] GDMA containing 0.25% CPQ and 0.05% BHT As a comparison, two additional Paste I formulations, Paste Ih and Paste Ii, were prepared by combining the ingredients set out in TABLE VII, except that for Paste Ih allantoin ascorbate (prepared according to the procedure of Example 1 of U.S. Pat. No. 3,954,989) was substituted for the unmodified ascorbic acid and for Paste Ii the aluminum ascorbate of PREPARATORY EXAMPLE 1 was substituted for the unmodified ascorbic acid.

The three Paste I formulations were independently hand-loaded into opaque polyethylene syringes and degassed. Each Paste I was independently mixed with an equal amount of Paste IIb which was formed by combining the ingredients set out below in TABLE VIII.

TABLE VIII

| Ingredient | g |
| --- | --- |
| Glass of PREP. EX. 6 | 32 |
| GDMA | 8 |
| $K_2S_2O_8$ CAB Encapsulated | 0.512 |
| DPI | 0.4 |
| CPQ | 0.1 |

Disks of each Paste I:Paste IIb formulation were prepared and color coordinates measured as described in EXAMPLE 3. Then the syringes containing the remainder of Paste Ig, Paste Ih and Paste Ii were placed in a 45° C. oven.

On day 5, the Paste I formulations were removed from the oven and independently mixed with an equal amount of Paste IIb. Disks of each composition were prepared and color coordinates measured as detailed in EXAMPLE 3. The remainder of each Paste I formulation was returned to the 45° C. oven and the procedure of disk preparation and color coordinate measurement repeated on day 10.

Set out below in TABLE IX are the Paste I formulations, the number of days the Paste I formulation was aged at 45° C., the L*, a* and b* reflection color coordinates and the $\Delta E^*_{ab}$ color value for each Paste I:Paste IIb composition.

TABLE IX

| Paste I Composition | Day | Color Coordinates | | | |
| --- | --- | --- | --- | --- | --- |
| | | L* | a* | b* | $\Delta E_{ab}$* |
| Paste Ig | 0 | 91.69 | −3.30 | 27.56 | |
| | 5 | 92.64 | −2.60 | 23.98 | 3.77 |
| | 10 | 75.88 | −2.72 | 15.04 | 20.17 |
| Paste Ih | 0 | 92.28 | −3.12 | 23.61 | |
| | 5 | 92.61 | −2.79 | 24.26 | 0.81 |
| | 10 | 75.54 | −2.82 | 16.77 | 18.08 |
| Paste Ii | 0 | 91.86 | −3.80 | 27.29 | |
| | 5 | 91.84 | −3.52 | 27.93 | 0.70 |
| | 10 | 91.83 | −2.95 | 31.14 | 3.94 |

The data in TABLE IX show that both the Paste Ih:Paste IIb and the Paste Ii:Paste IIb compositions exhibited excellent color stability after 5 days aging at 45° C. Already by day 5, the Paste Ig:Paste IIb composition had noticeably yellowed. On day 5, it was observed that the Paste Ih composition contained localized areas wherein the composition had gelled, failing to maintain its pre-aged consistency. However, by day 10, only the Paste Ii:Paste IIb composition continued to exhibit excellent color stability. The Paste Ii composition contained the aluminum ascorbate, whereas the Paste Ih composition contained the allantoin ascorbate.

EXAMPLE 6

The ingredients set out below in TABLE X were combined to form Paste Ij.

TABLE X

| Ingredient | g |
| --- | --- |
| Glass of PREP. EX. 6 | 77.6 |
| GDMA* | 19.8 |
| $Na_2S_2O_5$ | 1.6 |
| Aluminum Ascorbate of PREPARATORY EXAMPLE 1 | 1.0 |

*GDMA containing 1% DPI, 0.25% CPQ and 0.05% BHT

Paste Ij was hand-loaded into an opaque polyethylene syringe and degassed. Paste Ij was mixed with an equal amount of Paste IIc which was formed by combining the ingredients set out below in TABLE XI.

TABLE XI

| Ingredient | % |
| --- | --- |
| Filler of PREP. EX. 7 | 68.1 |
| Copolymer[1] | 24 |
| GDMA[2] | 6.2 |
| Cumene Hydroperoxide | 1.7 |

[1] Ethylenically unsaturated acidic copolymer prepared like the precipitated dry polymer of EXAMPLE 11 of U.S. Pat. No. 5,130,347 containing 26.4% water, 20% HEMA, 6.5% 1-tartaric acid and 0.1% BHT
[2] GDMA containing 0.25% CPQ and 0.005% BHT Disks of Paste Ij:Paste IIc were prepared and color coordinates measured as described in EXAMPLE 3. Then the syringe containing the remainder of Paste Ij was placed in a 45° C. oven.

On day 6, the Paste Ij formulation was removed from the oven and mixed with an equal amount of Paste IIc. Disks were prepared and color coordinates measured as detailed in EXAMPLE 3. The remainder of Paste Ij was returned to the 45° C. oven and the procedure of disk preparation and color coordinate measurement repeated on day 14.

Set out below in TABLE XII are the Paste Ij:Paste IIc formulation, the number of days the Paste Ij formulation was aged at 45° C., the L*, a* and b* reflection color coordinates and the $\Delta E^*_{ab}$ color value for the Paste Ij:Paste IIc composition.

TABLE XII

| Paste Ij: Paste IIc | Day | Color Coordinates | | | |
| --- | --- | --- | --- | --- | --- |
| | | L* | a* | b* | $\Delta E_{ab}$* |
| | 0 | 91.44 | −1.38 | 22.50 | |
| | 6 | 91.36 | −6.70 | 22.49 | 0.69 |
| | 14 | 92.45 | −2.02 | 22.82 | 1.24 |

The data in TABLE XII show the excellent color stability of a paste:paste composition containing the aluminum ascorbate of PREPARATORY EXAMPLE 1 as the reducing agent and cumene hydroperoxide as the oxidizing agent. Even after 14 days at 45° C., the composition maintained excellent color stability.

What is claimed:

1. A curable dental composition, comprising:
   a) a compound having an ethylenically unsaturated moiety,
   b) an oxidizing agent, and
   c) metal complexed ascorbic acid, wherein the ascorbic acid is complexed with a metal selected from the group consisting of transition metals and metals of group IIIB.

2. The composition of claim 1, wherein the ethylenically unsaturated moiety comprises an acrylate or methacrylate.

3. The composition of claim 1, wherein the metal complexed ascorbic acid is zirconium or aluminum ascorbate.

4. The composition of claim 1, further comprising a photoinitiator.

5. The composition of claim 1, further comprising an acid-reactive filler or a filler that is not reactive with acid.

6. The composition of claim 1, wherein the $\Delta E^*_{ab}$ value of a cured sample after aging at 45° C. for 5 days is less than the $\Delta E^*_{ab}$ value of a similar sample containing unmodified ascorbic acid.

7. The composition of claim 6, wherein the $\Delta E^*_{ab}$ value of a cured sample after aging at 45° C. for 5 days is less than about 5.

8. The composition of claim 5, wherein the reactive filler comprises fluoroaluminosilicate glass.

9. The composition of claim 1, wherein the polymer comprises a homopolymer or copolymer of an alkenoic acid.

10. The composition of claim 1, wherein the oxidizing agent is selected from the group consisting of sodium persulfate, potassium persulfate, ammonium persulfate, alkyl ammonium persulfate, benzoyl peroxide, cumene hydroperoxide, tert-butyl hydroperoxide, tert-amyl hydroperoxide, 2,5-dihydroperoxy-2,5-dimethylhexane, salts of cobalt (III) or iron (III), hydroxylamine, perboric acid and its salts, salts of permanganate anion, and combinations thereof.

11. The composition of claim 10, wherein the oxidizing agent comprises potassium persulfate or cumene hydroperoxide.

12. The composition of claim 1, wherein the metal complexed ascorbic acid comprises zirconium or aluminum ascorbate.

13. The composition of claim 1, wherein the composition is a two part paste:paste formulation.

14. The composition of claim 13, wherein the paste:paste formulation comprises a first part that contains water and a second part that is substantially free of water.

15. The composition of claim 14, wherein the first part comprises at least one of the metal complexed ascorbic acid and the oxidizing agent.

16. The composition of claim 14, wherein the second part comprises at least one of the metal complexed ascorbic acid and the oxidizing agent.

17. The composition of claim 14, wherein the first part comprises the metal complexed ascorbic acid and the second part comprises the oxidizing agent.

18. The composition of claim 1, further comprising a photoinitiator.

19. The composition of claim 1, further comprising a filler that is not reactive with acid.

20. The composition of claim 1, wherein the $\Delta E^*_{ab}$ value of a cured sample after aging at 45° C. for 5 days is less than the $\Delta E^*_{ab}$ value of a similar sample containing unmodified ascorbic acid.

21. The composition of claim 20, wherein the $\Delta E^*_{ab}$ value of a cured sample after aging at 45° C. for 5 days is less than about 5.

* * * * *

UNITED STATES PATENT AND TRADEMARK OFFICE
CERTIFICATE OF CORRECTION

PATENT NO.: 5,501,727

DATED: March 26, 1996

INVENTOR(S): Bing Wang and Sumita B. Mitra

It is certified that error appears in the above-identified patent and that said Letters Patent is hereby corrected as shown below:

Column 15, Lines 11 and 12, delete "of group IIIB" and insert --selected from the group consisting of B, A1, Ga, In and Tl --

Signed and Sealed this

Twenty-first Day of April, 1998

Attest:

BRUCE LEHMAN

Attesting Officer

Commissioner of Patents and Trademarks